(12) United States Patent
Nagamatsu et al.

(10) Patent No.: US 10,596,083 B2
(45) Date of Patent: Mar. 24, 2020

(54) COMPOSITE PARTICLES BASED ON MINERAL UV-SCREENING AGENT AND PERLITE; COSMETIC OR DERMATOLOGICAL COMPOSITIONS CONTAINING THE SAME

(71) Applicant: L'OREAL, Paris (FR)

(72) Inventors: Yasuko Nagamatsu, Tokyo (JP); Didier Candau, Bievres (FR); Benjamin Keufer, Shanghai (CN); Chong Wei Zhang, Shanghai (CN)

(73) Assignee: L'OREAL, Paris (FR)

( * ) Notice: Subject to any disclaimer, the term of this patent is extended or adjusted under 35 U.S.C. 154(b) by 122 days.

(21) Appl. No.: 14/893,243

(22) PCT Filed: May 23, 2014

(86) PCT No.: PCT/EP2014/060709
§ 371 (c)(1),
(2) Date: Nov. 23, 2015

(87) PCT Pub. No.: WO2014/191324
PCT Pub. Date: Dec. 4, 2014

(65) Prior Publication Data
US 2016/0106642 A1   Apr. 21, 2016

(30) Foreign Application Priority Data

May 29, 2013 (FR) ..................................... 13 54871

(51) Int. Cl.
| | | |
|---|---|---|
| *A61K 8/02* | (2006.01) | |
| *A61K 8/26* | (2006.01) | |
| *A61K 8/29* | (2006.01) | |
| *A61Q 17/04* | (2006.01) | |
| *A61K 8/25* | (2006.01) | |
| *C09C 1/40* | (2006.01) | |

(52) U.S. Cl.
CPC .............. *A61K 8/25* (2013.01); *A61K 8/0241* (2013.01); *A61K 8/0279* (2013.01); *A61K 8/26* (2013.01); *A61K 8/29* (2013.01); *A61Q 17/04* (2013.01); *C09C 1/405* (2013.01); *A61K 2800/413* (2013.01); *A61K 2800/621* (2013.01); *A61K 2800/651* (2013.01); *C01P 2004/62* (2013.01)

(58) Field of Classification Search
None
See application file for complete search history.

(56) References Cited

U.S. PATENT DOCUMENTS

| | | | | |
|---|---|---|---|---|
| 8,585,818 | B1* | 11/2013 | Jones | .................... C09C 1/0015 106/31.9 |
| 2011/0269845 | A1* | 11/2011 | Bujard | .................. C09C 1/0015 514/770 |

FOREIGN PATENT DOCUMENTS

| | | | | |
|---|---|---|---|---|
| EP | 0558881 | A2 | 9/1993 | |
| FR | 2881643 | A1 | 8/2006 | |
| FR | 2911496 | A1 * | 7/2008 | .............. A61K 8/06 |
| FR | 2982148 | A1 | 5/2013 | |
| JP | 62198608 | A2 * | 9/1987 | .............. A61K 7/00 |
| WO | WO2011101239 | A2 * | 8/2011 | .............. A61K 8/25 |
| WO | WO 2013068236 | A1 * | 5/2013 | ........... A61K 8/0225 |

OTHER PUBLICATIONS

Habibi et al., "Synthesis and Characterization of Titania Nanoparticles on the Surface of Microporous Perlite Using Sol-Gel Method: Influence of Titania Precursor on Characteristics", J Inorg Organomet Polym (2011) 21:634-639.*
Horiba (http://www.horiba.com/scientific/products/particle-characterization/applications/what-is-a-nanoparticle/, last visit Sep. 16, 2016).*
Hosseini et al., "Immobilization of TiO2 on perlite granules for photocatalytic degradation of pheno", Applied Catalysis B: Environmental 74 (2007) 53-62. I.*
Perlite.info. ([retrieved form on-line website: http://www.perlite.info/hbk/0031401.htm, pp. 1-3, copyright 1996-2011, last visit Sep. 29, 2017]). (Year: 2011).*
[Retrieved from on-line website: https://www.google.com/search?biw=1280&bih=662&ei=EWSDWsOtJ6qe_QbCy7KgDA&q=include+meaning&oq=include+meaning&gs . . . , last visit date 2018] (Year: 2018).*

* cited by examiner

*Primary Examiner* — Kyung S Chang
(74) *Attorney, Agent, or Firm* — Polsinelli PC

(57) ABSTRACT

The present invention relates to novel composite particles based on mineral UV-screening agent and perlite. The present invention also relates to a composition comprising, in a cosmetically acceptable medium, at least composite particles for screening out UV radiation, based on mineral UV-screening agent and perlite. The invention also relates to a cosmetic process for caring for and/or making up human keratin materials, especially bodily or facial skin or the hair, comprising at least the application, to the surface of the keratin material, of at least one composition as defined previously. The invention also relates to a non-therapeutic cosmetic process for limiting the darkening of the skin and/or improving the colour and/or uniformity of the complexion, comprising the application, to the surface of the keratin material, of at least one composition as defined previously. The invention also relates to a non-therapeutic cosmetic process for preventing and/or treating the signs of ageing of a keratin material, comprising the application, to the surface of the keratin material, of at least one composition as defined previously.

19 Claims, No Drawings

COMPOSITE PARTICLES BASED ON MINERAL UV-SCREENING AGENT AND PERLITE; COSMETIC OR DERMATOLOGICAL COMPOSITIONS CONTAINING THE SAME

CROSS REFERENCE TO RELATED APPLICATIONS

This application is a National Phase filing under 35 U.S.C. § 371 of PCT/EP2014/060709 filed on May 23, 2014; and this application claims priority to Application No. 1354871 filed in France on May 29, 2013 under 35 U.S.C. § 119. The entire contents of each application are hereby incorporated by reference.

The present invention relates to novel composite particles based on mineral UV-screening agent and perlite.

The present invention also relates to a composition comprising, in a cosmetically acceptable medium, at least:
a) composite particles with a mean size of greater than 0.1 µm, containing:
  i) a matrix consisting of perlite particles and
  ii) at least one mineral UV-screening agent with a mean elementary size of less than 0.1 µm.

The invention also relates to a cosmetic process for caring for and/or making up human keratin materials, especially bodily or facial skin or the hair, comprising at least the application, to the surface of the keratin material, of a composition as defined previously.

The invention also relates to a non-therapeutic cosmetic process for limiting the darkening of the skin and/or improving the colour and/or uniformity of the complexion, comprising the application, to the surface of the keratin material, of a composition as defined previously.

The invention also relates to a non-therapeutic cosmetic process for preventing and/or treating the signs of ageing of a keratin material, comprising the application, to the surface of the keratin material, of a composition as defined previously.

It is known that UV radiation with wavelengths of between 280 nm and 400 nm permits tanning of the human epidermis and that radiation with wavelengths of between 280 and 320 nm, known as UVB rays, harms the development of a natural tan. Exposure is also liable to bring about a detrimental change in the biomechanical properties of the epidermis, which is reflected by the appearance of wrinkles, leading to premature ageing of the skin.

It is also known that UVA rays with wavelengths of between 320 and 400 nm penetrate more deeply into the skin than UVB rays. UVA rays bring about immediate and persistent tanning of the skin. Daily exposure to UVA rays, even of short duration, under normal conditions can result in damage to the collagen fibres and the elastin, which is reflected by a modification to the microrelief of the skin, the appearance of wrinkles and uneven pigmentation (liver spots, heterogeneity of the complexion).

Many photoprotective compositions have been proposed to date to overcome the effects induced by UVA and/or UVB radiation. They generally contain organic or mineral UV-screening agents, which function according to their own chemical nature and according to their own properties by absorption, reflection or scattering of the UV radiation. They generally contain mixtures of liposoluble organic screening agents and/or of water-soluble UV-screening agents combined with metal oxide pigments such as titanium dioxide or zinc oxide. The antisun compositions commonly used in the antisun cosmetic market are generally in the form of oil, an oil-in-water emulsion (stabilized dispersion of an oily phase in an aqueous phase) or a water-in-oil emulsion (stabilized dispersion of an aqueous phase in an oily phase) comprising at least one oily phase comprising solvents and oils. These compositions often have a tendency to produce on the skin after application both a shiny, lustrous effect that consumers find unattractive and an uncomfortable greasy feel.

To overcome this problem, one solution would consist in adding to these compositions matting fillers such as the perlite particles known for these properties in patents FR 2 881 643 and FR 2 924 929. However, the Applicant has found in the course of its research that these antisun compositions comprising these perlite particles in loose form, organic screening agents and metal oxide pigments do not satisfactorily reduce the shininess and the greasy feel obtained on the skin after application.

There is thus still a need to find novel systems for screening out UV radiation efficiently and for substantially reducing, after application to the surface of a human keratin material, the shininess and the greasy feel.

The Applicant has discovered, surprisingly, that this objective can be achieved by using novel composite particles for screening out UV radiation based on mineral UV-screening agent and perlite particles.

This discovery forms the basis of the present invention.

The present invention relates to novel composite particles containing at least:
i) a matrix consisting of perlite particles and
ii) one mineral UV-screening agent with a mean elementary size of less than 0.1 µm.

The present invention also relates to a composition comprising, in a cosmetically acceptable medium, at least composite particles containing at least:
i) a matrix consisting of perlite particles and
ii) one mineral UV-screening agent with a mean elementary size of less than 0.1 µm.

The invention also relates to a cosmetic process for caring for and/or making up human keratin materials, especially bodily or facial skin or the hair, comprising at least the application, to the surface of the keratin material, of a composition as defined previously.

The invention also relates to a non-therapeutic cosmetic process for limiting the darkening of the skin and/or improving the colour and/or uniformity of the complexion, comprising the application, to the surface of the keratin material, of a composition as defined previously.

The invention also relates to a non-therapeutic cosmetic process for preventing and/or treating the signs of ageing of a keratin material, comprising the application, to the surface of the keratin material, of a composition as defined previously.

The invention also relates to a cosmetic process for making the skin matt and/or for reducing its shininess and/or reducing the greasy effect, comprising the topical application, to the skin, of a composition as defined previously.

The term "human keratin materials" means the skin (of the body, face and around the eyes), hair, eyelashes, eyebrows, bodily hair, nails, lips or mucous membranes.

The term "cosmetically acceptable medium" means any medium that is compatible with the skin and/or its integuments, which has a pleasant colour, odour and feel, and which does not cause any unacceptable discomfort (stinging, tautness or redness) liable to discourage the consumer from using this composition.

The term "mineral UV-screening agent" means a molecule not comprising any carbon atoms in its structure and capable of screening out UV radiation between 280 and 400 nm.

The term "mean size" means the mean size or mean diameter that can be determined by calculating the mean of the dimensions of approximately a hundred particles on an image with a scanning electron microscope.

The term "mean elementary size" means the size of non-aggregated particles.

Composite Particles

The composite particles in accordance with the invention comprise a matrix consisting of perlite particles and at least one mineral UV-screening agent.

The composite particles that may be used according to the invention may be monolayer or multilayer particles. The composite particles that may be used according to the invention may be spherical or non-spherical particles.

The term "spherical" means that the particle has a sphericity index, i.e. the ratio between its largest diameter and its smallest diameter, of less than 1.2.

The term "non-spherical" refers to particles in three dimensions (length, width and thickness or height) for which the ratio of the longest dimension to the shortest dimension is greater than 1.2. The dimensions of the particles of the invention are evaluated by scanning electron microscopy and image analysis. They comprise particles of parallelepipedal shape (rectangular or square surface), discoid shape (circular surface) or ellipsoid shape (oval surface), characterized by three dimensions: a length, a width and a height. When the shape is circular, the length and the width are identical and correspond to the diameter of a disc, whereas the height corresponds to the thickness of the disc. When the surface is oval, the length and the width correspond, respectively, to the large axis and the small axis of an ellipse and the height corresponds to the thickness of the elliptic disc formed by the platelet. When it is a parallelepiped, the length and the width may be of identical or different dimensions: when they are of the same dimension, the shape of the surface of the parallelepiped is a square; in the contrary case, the shape is rectangular. As regards the height, it corresponds to the thickness of the parallelepiped.

The dimensions of the particles of the invention are evaluated by scanning electron microscopy and image analysis.

According to a first variant, the composite particles contain a matrix consisting of perlite particles, in which matrix particles of mineral UV-screening agent are included. According to this embodiment, the matrix has inclusions and particles of mineral UV-screening agent are placed in the inclusions of the matrix.

According to a second variant, the composite particles contain a matrix consisting of perlite particles, the said matrix being partially or totally covered with at least one layer of mineral UV-screening agent which may be connected to the matrix by means of a binder.

Preferentially, when the composite particles of the invention are spherical, their mean size preferably ranges between 0.1 and 30 µm.

Preferentially, when the composite particles of the invention are non-spherical, they are characterized by a mean size of from 0.1 to 30 µm.

The dimensions of the particles of the invention are evaluated by scanning electron microscopy and image analysis.

The non-spherical composite particles that may be used according to the invention are preferably platelet-shaped.

The term "platelet-shaped" is understood to mean a parallelepipedal shape.

The platelet-shaped composite particles preferably have a mean size of from 0.1 to 30 µm.

The composite UV-screening agent(s) according to the invention are preferably present in the compositions of the invention in concentrations ranging from 1% to 70% by weight, preferably from 1.5% to 50% by weight and preferably from 2% to 40% by weight, relative to the total weight of the cosmetic composition.

a) Mineral UV-screening Agents

The mineral UV-screening agents used in accordance with the present invention are metal oxide pigments. More preferentially, the mineral UV-screening agents of the invention are metal oxide particles with a mean elementary particle size of less than 0.1 µm.

The mineral UV-screening agent is generally chosen from metal oxides, preferably titanium, zinc or iron oxides or mixtures thereof and more particularly from titanium dioxide and zinc oxide, and mixtures thereof. In a particularly preferred manner, the mineral UV-screening agent is titanium dioxide ($TiO_2$); the said metal oxides may optionally be treated with at least one surface-treatment agent.

In particular, the titanium dioxide ($TiO_2$) may be in rutile and/or anatase form and/or in an amorphous form.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

According to the invention, coated or uncoated titanium oxide pigments are particularly preferred.

The mass content of mineral UV-screening agent in the composite particles of the invention is preferably from 1% to 90% by weight, preferably from 2% to 80% by weight and better still from 3% to 70% by weight, relative to the total weight of a composite particle.

b) Perlite Particles

Perlite is a natural glass of volcanic origin, of glossy black or light-grey colour, resulting from the rapid cooling of lava, and which is in the form of small particles resembling pearls.

The perlites which can be used according to the invention are generally aluminosilicates of volcanic origin and have the composition:

70.0-75.0% by weight of silica $SiO_2$
12.0-15.0% by weight of aluminium oxide $Al_2O_3$
3.0-5.0% of sodium oxide $Na_2O$
3.0-5.0% of potassium oxide $K_2O$
0.5-2% of iron oxide $Fe_2O_3$
0.2-0.7% of magnesium oxide MgO
0.5-1.5% of calcium oxide CaO
0.05-0.15% of titanium dioxide $TiO_2$ Preferentially, the perlite particles used according to the invention will be in porous expanded form.

The perlite is ground, dried and then calibrated in a first stage. The product obtained, known as perlite ore, is grey-coloured and has a size of the order of 100 µm. The perlite ore is subsequently expanded (1000° C./2 seconds) to give more or less white particles. When the temperature reaches 850-900° C., the water trapped in the structure of the material evaporates and brings about the expansion of the material, with respect to its original volume. The expanded perlite particles in accordance with the invention may be obtained via the expansion process described in patent U.S. Pat. No. 5,002,698.

Preferably, the perlite particles used will be ground; in this case, they are known as Expanded Milled Perlite (EMP).

They preferably have a particle size defined by a median diameter $D_{50}$ ranging from 0.5 to 50 µm and preferably from 0.5 to 40 µm.

Preferably, the perlite particles according to the invention have a particle size distribution such that at least 50% of the particles are less than 20 µm in size. In addition, they preferentially have a particle size distribution such that 90% by weight of the particles are less than 55 µm in size and preferably less than 40 µm in size. It is moreover preferred for 90% by weight of the particles to be greater than 5 µm in size.

Preferably, the perlite particles used have an untamped apparent density at 25° C. ranging from 10 to 400 kg/m³ (standard DIN 53468) and preferably from 10 to 300 kg/m³.

The expanded perlite particles sold under the trade names Optimat 1430 OR® and Optimat 2550® by the company World Minerals, or the commercial products GK-110 Thin® and GK-110 Extra Thin® by the company Langfang Xindazhong Filter and the company Henan Zhongnan Filter Aid, will in particular be used.

The mass content of perlite in the composite particles of the invention is preferably from 10% to 99% by weight, more preferentially from 20% to 98% by weight and even more preferentially from 30% to 97% by weight, relative to the total weight of a composite particle.

c) Preparation of the Composite Particles

The composite particles in accordance with the present invention may be obtained according to the process described in patent FR 2 882 371 B1, which consists in impregnating perlite particles with an aqueous suspension of metal oxide particles such as titanium dioxide with a mean elementary particle size of less than 0.1 µm, and then in reducing the precursors in the said material forming the matrix; the impregnation being performed under saturating vapour pressure and at the reflux point of the solution of one or more metal oxide precursors (for example titanium dioxide), and the reduction being performed radiolytically.

The metal oxide precursors may be chosen from mineral salts (for example sulfates or perchlorates), organic salts (for example formates or neodecanoates) or organometallic compounds.

The precursor solution may also contain an oxidizing-radical interceptor, which intercepts the oxidizing radicals formed in the solution during the irradiation, which avoids the oxidation of the colloidal particles produced. The oxidizing-radical interceptor is preferably chosen from primary alcohols, secondary alcohols and formates.

The composite particles based on perlite and mineral screening agent may also be obtained according to the process described in patent application WO 2006/083 326, which consists in generating a gaseous dispersion as a flow comprising droplets of a precursor support dispersed in a gas phase. The precursor support contains a liquid vehicle and at least one metal oxide precursor with an elementary size of less than 0.1 µm and a perlite-based matrix. The composite particles are formed from the gaseous dispersion by eliminating a portion of the liquid vehicle of the droplets of the precursor medium.

According to a particularly preferred form of the invention, the composite particles may also be prepared according to the process described in patent application KR 1020000069638, which consists, according to a sol-gel method, in mixing in water an aqueous suspension of a metal alkoxide (especially of a titanium alkoxide such as titanium tetra-n-butoxide, also known as tetra-n-butyl titanate (TNBT)) with a perlite matrix and in reacting the metal alkoxide by hydrolysis for a time preferably ranging from 1 to 8 hours at a temperature preferably ranging from 30 to 78° C. Next, the suspension thus obtained is filtered, washed and dried to produce a composite powder of perlite coated with metal oxide. To improve the uniformity of the coating of mineral screening agent on the perlite particles, the composite particles obtained may be reacted, according to the same process, with the suspension of metal alkoxide.

According to another particular form of the invention, the composite particles may also be prepared according to the process described in patent U.S. Pat. No. 6,447,759, which consists in preparing a suspension of perlite particles, adding a complexing agent to the suspension, adding a precursor metal oxide salt of the mineral screening agent and an alkaline agent of the carbonate type to form basic metal oxide carbonate particles on the perlite matrix, and calcining the composite particles.

According to a particular form of the invention, the composite particles may also be prepared according to the process described in patent application JP 2008115161, which consists in preparing a suspension of perlite particles at acidic pH in the presence of hydrochloric acid. The metal oxide particles constituting the mineral screening agent are then added. At acidic pH, a flocculant such as calcium chloride is added to obtain the composite particles.

According to another particular form of the invention, the composite particles of the invention may be prepared by subjecting the perlite particles and the mineral screening agent(s) as defined previously to a mechanochemical melting process.

A mechanochemical melting process means a process in which a mechanical force such as an impact, a friction force or a shear force is exerted on a plurality of compounds, to produce partial melting of the various compounds.

The mechanochemical melting process may be performed, for example, with a machine comprising a rotary chamber and an internal fixed part with a scraper, such as the mechanofusion device of the Japanese commercial brand Hosokawa Micron Corporation®.

It is preferable to use a hybridizer process as mechanochemical melting process.

The hybridizer process was developed in the 1980s. The hybridizer process is a type of mechanochemical melting process in which a strong mechanical force is applied to a plurality of particles in order to produce a mechanochemical reaction and to form a composite particle.

According to the hybridizer process, the mechanical force is exerted by a high-speed rotor which may have a diameter from 10 cm to 1 m and which can rotate at a speed from 1000 to 100 000 rpm. Thus, the hybridizer process may be defined as a mechanochemical melting process using a high-speed rotor. The hybridizer process is performed in the presence of air or under dry conditions. Specifically, on account of the high speed of the rotor, a high-speed air stream may be produced close to the rotor. Some liquid materials can be subjected to the hybridizer process in the presence of solid materials. The term "hybridizer process" has been used as the technical term in the present description.

The hybridizer process may be performed using a hybridization system of the Japanese brand Nara Machinery®, in which the perlite particles and those of the mineral screening agent are introduced into a hybridizer equipped with a high-speed rotor having a plurality of blades in a dry chamber. The particles are dispersed in the chamber and mechanical and thermal energy (i.e. compression, friction, shear force) are exerted on the particles for a short period of time such as from 1 to 10 minutes, preferably from 1 to 5 minutes. This results in particles of one type (i.e. fine particles) integrated into or attached to particles of another type (core particles) so as to form the composite particles in accordance with the invention. It is preferable for the particles to have been subjected to one or more electrostatic treatments such as buffeting to form an "ordered mixture" in which one type of particle is spread out to cover the other type of particle. The hybridizer process may also be performed by using a theta composter of the Japanese brand Tokuju Corporation®.

The hybridizer process may be performed with a Composi Hybrid® or Mechano Hybrid® device sold by the company Nippon Coke.

According to the present invention, the perlite particles and the mineral screening agent(s) may be introduced into a hybridizer to form a composite pigment. The hybridizer process may be performed using a rotor rotating at 8000 rpm (100 m/sec) for approximately 3 minutes.

Furthermore, the hybridizer process can create an ordered assembly (uniform coating) of the mineral UV-screening agent(s) on the perlite particle and produce strong bonds on the surface of the perlite particle and the coating layer comprising the mineral UV-screening agent(s).

It should be noted that the hybridizer process is very different from other processes using, for example, a ball mill and a jet mill. Specifically, ball mills bring about spraying or agglomeration of the particles forming the core of the composite, and jet mills bring about spraying of the said particles, making it difficult to uniformly coat the fine particles onto the particles forming the core of the composite.

Oily Phase

The compositions in accordance with the invention preferably comprise at least one oily phase.

For the purposes of the invention, the term "oily phase" is intended to mean a phase comprising at least one oil and all of the liposoluble and lipophilic ingredients and the fatty substances used for the formulation of the compositions of the invention.

The term "oil" means any fatty substance that is in liquid form at room temperature (20-25° C.) and at atmospheric pressure (760 mmHg).

An oil that is suitable for use in the invention may be volatile or non-volatile.

An oil that is suitable for use in the invention may be chosen from hydrocarbon-based oils, silicone oils and fluoro oils, and mixtures thereof.

A hydrocarbon-based oil that is suitable for use in the invention may be an animal hydrocarbon-based oil, a plant hydrocarbon-based oil, a mineral hydrocarbon-based oil or a synthetic hydrocarbon-based oil.

An oil that is suitable for use in the invention may be advantageously chosen from mineral hydrocarbon-based oils, plant hydrocarbon-based oils, synthetic hydrocarbon-based oils and silicone oils, and mixtures thereof.

For the purposes of the present invention, the term "silicone oil" is intended to mean an oil comprising at least one silicon atom, and in particular at least one Si—O group.

The term "hydrocarbon-based oil" is intended to mean an oil comprising mainly hydrogen and carbon atoms.

The term "fluoro oil" is intended to mean an oil comprising at least one fluorine atom.

A hydrocarbon-based oil that is suitable for use in the invention may also optionally comprise oxygen, nitrogen, sulfur and/or phosphorus atoms, for example in the form of hydroxyl, amine, amide, ester, ether or acid groups, and in particular in the form of hydroxyl, ester, ether or acid groups.

The oily phase generally comprises, in addition to the lipophilic UV-screening agent(s), at least one volatile or non-volatile hydrocarbon-based oil and/or one volatile and/or non-volatile silicone oil.

For the purposes of the invention, the term "volatile oil" means an oil that is capable of evaporating on contact with the skin or the keratin fibre in less than one hour, at room temperature and atmospheric pressure. The volatile oil(s) of the invention are volatile cosmetic oils which are liquid at room temperature and which have a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

Hydrocarbon-based Oils

Mention may in particular be made, as non-volatile hydrocarbon-based oils which can be used according to the invention, of:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheatgerm oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame oil, marrow oil, blackcurrant oil, evening primrose oil, millet oil, barley oil, *quinoa* oil, rye oil, safflower oil, candlenut oil, passionflower oil and musk rose oil; or also caprylic/capric acid triglycerides, such as those sold by Stéarineries Dubois or those sold under the names Miglyol 810®, 812® and 818® by Dynamit Nobel;

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and squalane, and mixtures thereof;

(iv) synthetic esters, for instance oils of formula RCOOR' in which R represents a linear or branched fatty acid residue containing from 1 to 40 carbon atoms and R' represents a hydrocarbon-based chain that is in particular branched, containing from 1 to 40 carbon atoms, on condition that R+R' is ≥10, for instance purcellin oil (cetostearyl octanoate), isopropyl myristate, isopropyl palmitate, $C_{12}$-$C_{15}$ alkyl benzoate, such as the product sold under the trade name Finsolv TN® or Witconol TN® by the company Witco or Tegosoft TN® by the company Evonik Goldschmidt, 2-ethylphenyl benzoate, such as the commercial product sold under the name X-Tend 226® by the company ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name Dub Dis by the company Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by the company Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids such as oleic acid, linoleic acid or linolenic acid;

(vii) carbonates, such as dicaprylyl carbonate, such as the product sold under the name Cetiol CC® by the company Cognis;

(viii) fatty amides, such as isopropyl N-lauroyl sarcosinate, such as the product sold under the trade name Eldew SL 205® from Ajinomoto;

and mixtures thereof.

Among the non-volatile hydrocarbon-based oils that may be used according to the invention, preference will be given more particularly to glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, in particular octyldodecanol.

As volatile hydrocarbon-based oils that may be used according to the invention, mention may be made especially of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4, 6-pentamethylheptane), isodecane or isohexadecane, the oils sold under the Isopar or Permethyl trade names, branched $C_8$-$C_{16}$ esters, isohexyl neopentanoate, and mixtures thereof.

Mention may also be made of the alkanes described in the Cognis patent applications WO 2007/068 371 or WO 2008/ 155 059 (mixtures of distinct alkanes differing by at least one carbon). These alkanes are obtained from fatty alcohols, which are themselves obtained from coconut or palm oil. Mention may be made of the mixtures of n-undecane ($C_{11}$) and n-tridecane ($C_{13}$) obtained in Examples 1 and 2 of patent application WO 2008/155 059 from the company Cognis. Mention may also be made of n-dodecane ($C_{12}$) and n-tetradecane ($C_{14}$) sold by Sasol under the respective references Parafol 12-97® and Parafol 14-97®, and also mixtures thereof.

Other volatile hydrocarbon-based oils, for instance petroleum distillates, in particular those sold under the name Shell Solt® by the company Shell, may also be used. According to one embodiment, the volatile solvent is chosen from volatile hydrocarbon-based oils containing from 8 to 16 carbon atoms, and mixtures thereof.

b) Silicone Oils

The non-volatile silicone oils may be chosen in particular from non-volatile polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Examples of volatile silicone oils that may be mentioned include volatile linear or cyclic silicone oils, in particular those with a viscosity ≤8 centistokes ($8 \times 10^{-6}$ m$^2$/s) and in particular containing from 2 to 7 silicon atoms, these silicones optionally comprising alkyl or alkoxy groups containing from 1 to 10 carbon atoms. As volatile silicone oils that may be used in the invention, mention may be made in particular of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of volatile linear alkyltrisiloxane oils of general formula (I):

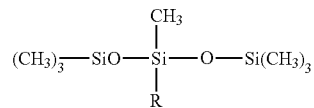

where R represents an alkyl group comprising from 2 to 4 carbon atoms, one or more hydrogen atoms of which can be replaced by a fluorine or chlorine atom.

Mention may be made, among the oils of general formula (I), of:

3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

Fluoro Oils

Use may also be made of volatile fluoro oils, such as nonafluoromethoxybutane, decafluoropentane, tetradecafluorohexane, dodecafluoropentane, and mixtures thereof.

An oily phase according to the invention may also comprise other fatty substances, mixed with or dissolved in the oil.

Another fatty substance that may be present in the oily phase may be, for example:

a fatty acid chosen from fatty acids comprising from 8 to 30 carbon atoms, such as stearic acid, lauric acid, palmitic acid and oleic acid;

a wax chosen from waxes such as lanolin, beeswax, carnauba or candelilla wax, paraffin waxes, lignite waxes, microcrystalline waxes, ceresin or ozokerite, or synthetic waxes, such as polyethylene waxes or Fischer-Tropsch waxes;

a gum chosen from silicone gums (dimethiconol);

a pasty compound, such as polymeric or non-polymeric silicone compounds, esters of a glycerol oligomer, arachidyl propionate, fatty acid triglycerides and derivatives thereof;

and mixtures thereof.

Preferentially, the overall oily phase, including all the lipophilic substances of the composition capable of being dissolved in this same phase, represents from 5% to 95% by weight and preferentially from 10% to 80% by weight, relative to the total weight of the composition.

Aqueous Phase

The compositions according to the invention may also comprise at least one aqueous phase.

The aqueous phase contains water and optionally other water-soluble or water-miscible organic solvents.

An aqueous phase that is suitable for use in the invention may comprise, for example, a water chosen from a natural spring water, such as water from La Roche-Posay, water from Vittel or waters from Vichy, or a floral water.

The water-soluble or water-miscible solvents that are suitable for use in the invention comprise short-chain monoalcohols, for example $C_1$-$C_4$ monoalcohols, such as ethanol or isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, glycerol and sorbitol, and mixtures thereof.

According to a preferred embodiment, use may more particularly be made of ethanol, propylene glycol, glycerol, and mixtures thereof.

According to one particular form of the invention, the overall aqueous phase, including all the hydrophilic substances of the composition capable of being dissolved in this same phase, represents from 5% to 95% by weight and preferential from 10% to 80% by weight, relative to the total weight of the composition.

Additives

The compositions according to the invention also preferably contain in loose form one or more organic UV-screening agents.

Organic UV-screening Agents

The organic UV-screening agents are chosen in particular from cinnamic compounds; anthranilate compounds; salicylic compounds; dibenzoylmethane compounds; benzylidenecamphor compounds; benzophenone compounds; β,β-diphenylacrylate compounds; triazine compounds; benzotriazole compounds; benzalmalonate compounds, in particular those cited in patent U.S. Pat. No. 5,624,663; benzimidazole derivatives; imidazoline compounds; bis-benzazolyl compounds, as described in patents EP 669 323 and U.S. Pat. No. 2,463,264; p-aminobenzoic acid (PABA) compounds; methylenebis(hydroxyphenylbenzotriazole) compounds, as described in patent applications U.S. Pat. Nos. 5,237,071, 5,166,355, GB 2 303 549, DE 197 26 184 and EP 893 119; benzoxazole compounds, as described in patent applications EP 0 832 642, EP 1 027 883, EP 1 300 137 and DE 101 62 844; screening polymers and screening silicones, such as those described in particular in patent application WO 93/04665; α-alkylstyrene-based dimers, such as those described in patent application DE 198 55 649; 4,4-diarylbutadiene compounds, as described in patent applications EP 0 967 200, DE 197 46 654, DE 197 55 649, EP-A-1 008 586, EP 1 133 980 and EP 133 981, and mixtures thereof.

As examples of organic photoprotective agents, mention may be made of those denoted hereinbelow under their INCI name:

Cinnamic Compounds:
ethylhexyl methoxycinnamate sold in particular under the trade name Parsol MCX® by DSM Nutritional Products,
isopropyl methoxycinnamate,
isoamyl p-methoxycinnamate sold under the trade name Neo Heliopan E 1000® by Symrise,
DEA methoxycinnamate,
diisopropyl methyl cinnamate,
glyceryl ethylhexanoate dimethoxycinnamate.

Para-Aminobenzoic Compounds:
PABA,
ethyl PABA,
ethyl dihydroxypropyl PABA,
ethylhexyl dimethyl PABA, sold in particular under the name Escalol 507® by ISP,
glyceryl PABA,
PEG-25 PABA, sold under the name Uvinul P 25® by BASF.

Salicylic Compounds:
Homosalate, sold under the name Eusolex HMS® by Rona/EM Industries,
ethylhexyl salicylate, sold under the name Neo Heliopan OS® by Symrise,
dipropylene glycol salicylate, sold under the name Dipsal® by Scher,
TEA salicylate, sold under the name Neo Heliopan TS® by Symrise.

Dibenzoylmethane Compounds:
butylmethoxydibenzoylmethane or Avobenzone, sold in particular under the trade name Parsol 1789® by DSM Nutritional Products.

β,β-Diphenylacrylate Compounds:
Octocrylene, sold in particular under the trade name Uvinul N 539® by BASF,
Etocrylene, sold in particular under the trade name Uvinul N 35® by BASF.

Benzophenone Compounds:
Benzophenone-1 sold under the trade name Uvinul 400® by BASF,
Benzophenone-2, sold under the trade name Uvinul D 50® by BASF,
Benzophenone-3 or Oxybenzone, sold under the trade name Uvinul M 40® by BASF,
Benzophenone-4, sold under the trade name Uvinul MS 40® by BASF,
Benzophenone-5,
Benzophenone-6 sold under the trade name Helisorb 11® by Norquay,
Benzophenone-8 sold under the trade name Spectra-Sorb UV-24® by American Cyanamid,
Benzophenone-9, sold under the trade name Uvinul DS 49® by BASF,
Benzophenone-12,
n-hexyl 2-(4-diethylamino-2-hydroxybenzoyl)benzoate, sold under the trade name
Uvinul A Plus® or, as a mixture with octyl methoxycinnamate, under the trade name Uvinul A Plus B® by BASF,
1,1'-(1,4-piperazinediyl)bis[1-[2-[4-(diethylamino)-2-hydroxybenzoyl]phenyl]methanone] (CAS 919803-06-8), such as described in patent application WO 2007/071 584; this compound advantageously being used in micronized form (mean size of 0.02 to 2 μm), which may be obtained, for example, according to the micronization process described in patent applications GB-A-2 303 549 and EP-A-893 119, and especially in the form of an aqueous dispersion.

Benzylidenecamphor Compounds:
3-benzylidenecamphor, manufactured under the name Mexoryl SD® by Chimex,
4-methylbenzylidenecamphor, sold under the name Eusolex 6300® by Merck,
benzylidenecamphorsulfonic acid, manufactured under the name Mexoryl SL® by Chimex,
camphor benzalkonium methosulfate, manufactured under the name Mexoryl SO® by Chimex,
terephthalylidenedicamphorsulfonic acid, manufactured under the name Mexoryl SX® by Chimex,
polyacrylamidomethylbenzylidenecamphor, manufactured under the name Mexoryl SW® by Chimex.

Phenylbenzimidazole Compounds:

phenylbenzimidazolesulfonic acid, sold in particular under the trade name Eusolex 232® by Merck.

Bis-benzazolyl Compounds:
disodium phenyl dibenzimidazole tetrasulfonate, sold under the trade name Neo Heliopan AP® by Haarmann and Reimer.

Phenylbenzotriazole Compounds:
Drometrizole trisiloxane, sold under the name Silatrizole® by Rhodia Chimie.

Methylenebis(hydroxyphenylbenzotriazole) Compounds:
methylenebis(benzotriazolyl)tetramethylbutylphenol, in particular in solid form, such as the product sold under the trade name Mixxim BB/100® by Fairmount Chemical, or in the form of an aqueous dispersion of micronized particles with a mean particle size ranging from 0.01 to 5 μm, more preferentially from 0.01 to 2 μm and more particularly from 0.020 to 2 μm, with at least one alkylpolyglycoside surfactant having the structure $C_nH_{2n+1}O(C_6H_{10}O_5)_xH$, in which n is an integer from 8 to 16 and x is the mean degree of polymerization of the $(C_6H_{10}O_5)$ unit and ranges from 1.4 to 1.6, as described in patent GB-A-2 303 549, sold in particular under the trade name Tinosorb M® by the company BASF, or in the form of an aqueous dispersion of micronized particles with a mean particle size ranging from 0.02 to 2 μm, more preferentially from 0.01 to 1.5 μm and more particularly from 0.02 to 1 μm, in the presence of at least one polyglyceryl mono($C_8$-$C_{20}$)alkyl ester with a degree of glycerol polymerization of at least 5, such as the aqueous dispersions described in patent application WO 2009/063 392.

Triazine Compounds:
- bis(ethylhexyloxyphenol)methoxyphenyltriazine, sold under the trade name Tinosorb S® by BASF,
- ethylhexyl triazone, sold in particular under the trade name Uvinul T150® by BASF,
- diethylhexyl butamido triazone, sold under the trade name Uvasorb HEB® by Sigma 3V,
- 2,4,6-tris(dineopentyl 4'-aminobenzalmalonate)-s-triazine,
- 2,4,6-tris(diisobutyl 4'-aminobenzalmalonate)-s-triazine,
- 2,4-bis(n-butyl 4'-aminobenzoate)-6-(aminopropyltrisiloxane)-s-triazine,
- 2,4-bis(dineopentyl 4'-aminobenzalmalonate)-6-(n-butyl 4'-aminobenzoate)-s-triazine,
- symmetrical triazine screening agents substituted with naphthalenyl groups or polyphenyl groups described in patent U.S. Pat. No. 6,225,467, patent application WO 2004/085 412 (see compounds 6 and 9) or the document "Symmetrical Triazine Derivatives", IP.COM IPCOM000031257 Journal, INC, West Henrietta, N.Y., US (20 Sep. 2004), in particular 2,4,6-tris(diphenyl) triazine and 2,4,6-tris(terphenyl)triazine, which is also mentioned in patent applications WO 06/035 000, WO 06/034 982, WO 06/034 991, WO 06/035 007, WO 2006/034 992 and WO 2006/034 985, these compounds advantageously being used in micronized form (mean particle size of 0.02 to 3 μm), which may be obtained, for example, according to the micronization process described in patent applications GB-A-2 303 549 and EP-A-893 119, and in particular in aqueous dispersion;
- silicone triazines substituted with two aminobenzoate groups, as described in patent EP 0 841 341, in particular 2,4-bis(n-butyl 4'-aminobenzalmalonate)-6-[(3-{1,3,3,3-tetramethyl-1-[(trimethylsilyl)oxy] disiloxanyl}propyl)amino]-s-triazine.

Anthranilic Compounds:
menthyl anthranilate, sold under the trade name Neo Heliopan MAO by Symrise.

Imidazoline Compounds:
ethylhexyl dimethoxybenzylidene dioxoimidazoline propionate.

Benzalmalonate Compounds:
polyorganosiloxane comprising benzalmalonate functional groups, such as Polysilicone-15, sold under the trade name Parsol SLX® by Hoffmann LaRoche.

4,4-Diarylbutadiene Compounds:
1,1-dicarboxy(2,2'-dimethylpropyl)-4,4-diphenylbutadiene.

Benzoxazole Compounds:
2,4-bis[5-(1,1-dimethylpropyl)benzoxazol-2-yl(4-phenyl) imino]-6-(2-ethylhexyl)imino-1,3,5-triazine, sold under the name Uvasorb K2A® by Sigma 3V.

The preferential organic screening agents are chosen from:
ethylhexyl methoxycinnamate,
butylmethoxydibenzoylmethane,
ethylhexyl salicylate,
Homosalate,
Octocrylene,
phenylbenzimidazolesulfonic acid,
Benzophenone-3,
Benzophenone-4,
Benzophenone-5,
n-hexyl 2-(4-diethylamino-2-hydroxybenzoyl)benzoate,
4-methyl benzylidenecamphor,
terephthalylidenedicamphorsulfonic acid,
disodium phenyl dibenzimidazole tetrasulfonate,
methylenebis(benzotriazolyl)tetramethylbutylphenol,
bis(ethylhexyloxyphenol)methoxyphenyltriazine
ethylhexyl triazone,
diethylhexyl butamido triazone,
2,4,6-tris(dineopentyl 4'-aminobenzalmalonate)-s-triazine,
2,4,6-tris(diisobutyl 4'-aminobenzalmalonate)-s-triazine,
2,4-bis(n-butyl 4'-aminobenzoate)-6-(aminopropyltrisiloxane)-s-triazine,
2,4-bis(dineopentyl 4'-aminobenzalmalonate)-6-(n-butyl 4'-aminobenzoate)-s-triazine,
2,4-bis(n-butyl 4'-aminobenzalmalonate)-6-[(3-{1,3,3,3-tetramethyl-1-[(trimethylsilyl)oxy]disiloxanyl}propyl) amino]-s-triazine,
2,4,6-tris(diphenyl)triazine,
2,4,6-tris(terphenyl)triazine,
Drometrizole trisiloxane,
Polysilicone-15,
1,1-dicarboxy(2,2'-dimethylpropyl)-4,4-diphenylbutadiene,
2,4-bis[4-[5-(1,1-dimethylpropyl)benzoxazol-2-yl]phenylimino]-6-[(2-ethylhexyl)imino]-1,3,5-triazine,
and mixtures thereof.

The particularly preferred organic screening agents are chosen from:
butylmethoxydibenzoylmethane,
ethylhexyl salicylate,
Homosalate,
Octocrylene,
n-hexyl 2-(4-diethylamino-2-hydroxybenzoyl)benzoate,
terephthalylidenedicamphorsulfonic acid,
bis(ethylhexyloxyphenol)methoxyphenyltriazine,
ethylhexyl triazone,
diethylhexyl butamido triazone,
2,4-bis(n-butyl 4'-aminobenzalmalonate)-6-[(3-{1,3,3,3-tetramethyl-1-[(trimethylsilyl)oxy]disiloxanyl}propyl) amino]-s-triazine,
Drometrizole trisiloxane,
and mixtures thereof.

The organic screening agents, when they are present, are present in contents ranging from 0.01% to 30% by weight and preferably from 0.1% to 20% by weight relative to the total weight of the composition of the invention.

The compositions in accordance with the present invention may also comprise conventional cosmetic adjuvants chosen in particular from organic solvents, ionic or nonionic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, basifying or acidifying agents or any other ingredient commonly used in the cosmetic and/or dermatological field.

Mention may be made, among organic solvents, of alcohols other than $C_1$-$C_4$ monoalkanols as defined above and in particular short-chain $C_2$-$C_8$ polyols, such as glycerol or diols, such as caprylyl glycol, 1,2-pentanediol, propanediol, butanediol, glycols and glycol ethers, such as ethylene glycol, propylene glycol, butylene glycol, dipropylene glycol or diethylene glycol.

Mention may be made, as thickeners, of carboxyvinyl polymers, such as the Carbopols® (Carbomers) and the Pemulens, such as Pemulen TR1® and Pemulen TR2® (acrylate/$C_{10}$-$C_{30}$ alkyl acrylate copolymer); polyacrylamides, for instance the crosslinked copolymers sold under the names Sepigel 305® (CTFA name: polyacrylamide/$C_{13-14}$ isoparaffin/Laureth 7) or Simulgel 600 (CTFA name: acrylamide/sodium acryloyldimethyl taurate copolymer/isohexadecane/polysorbate 80) by the company SEPPIC; 2-acrylamido-2-methylpropanesulfonic acid polymers and copolymers, optionally crosslinked and/or neutralized, such as the poly(2-acrylamido-2-methylpropanesulfonic acid) sold by the company Hoechst under the trade name Hostacerin AMPS® (CTFA name: ammonium polyacryloyldimethyl taurate) or Simulgel 800®, sold by the company SEPPIC (CTFA name: sodium polyacryloyldimethyl taurate/polysorbate 80/sorbitan oleate); copolymers of 2-acrylamido-2-methylpropanesulfonic acid and of hydroxyethyl acrylate, such as Simulgel NS® and Sepinov EMT 100, sold by the company SEPPIC; cellulose derivatives, such as hydroxyethylcellulose; polysaccharides and in particular gums, such as xanthan gum; water-soluble or water-dispersible silicone derivatives, such as acrylic silicones, polyether silicones and cationic silicones, and mixtures thereof.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include aqueous ammonia, alkali metal carbonates, alkanolamines, such as mono-, di- and triethanolamines and derivatives thereof, sodium hydroxide or potassium hydroxide.

Preferably, the cosmetic composition comprises one or more basifying agents selected from alkanolamines, in particular triethanolamine, and sodium hydroxide.

In the case of a direct emulsion, the pH of the composition in accordance with the invention is generally between 3 and 12 approximately, preferably between 5 and 11 approximately and even more particularly from 6 to 8.5.

Among the active agents for caring for keratin materials such as the skin, the lips, the scalp, the hair, the eyelashes or the nails, examples that may be mentioned include:

vitamins and derivatives or precursors thereof, alone or as mixtures;
antioxidants;
free-radical scavengers;
antipollution agents;
self-tanning agents;
antiglycation agents;
calmatives;
deodorants;
essential oils;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
refreshing agents;
tensioning agents;
matting agents;
depigmenting agents;
pro-pigmenting agents;
keratolytic agents;
desquamating agents;
moisturizers;
anti-inflammatory agents;
antimicrobial agents;
slimming agents;
agents acting on the energy metabolism of cells;
insect repellents;
substance P or CGRP antagonists;
hair-loss counteractants;
antiwrinkle agents;
antiageing agents.

A person skilled in the art will select the said active agent(s) according to the effect desired on the skin, the hair, the eyelashes, the eyebrows or the nails.

Needless to say, a person skilled in the art will take care to choose the abovementioned optional additional compound(s) and/or the amounts thereof so that the advantageous properties intrinsically attached to the compositions in accordance with the invention are not, or not substantially, detrimentally affected by the envisaged addition(s).

Galenical Forms

The compositions according to the invention may be prepared according to the techniques that are well known to those skilled in the art. They may in particular be in the form of a gel or a simple or complex emulsion (O/W, W/O, O/W/O or W/O/W), such as a cream, a milk or a cream gel.

They may also be in anhydrous form, for instance in the form of an oil. The term "anhydrous composition" means a composition containing less than 1% by weight of water, or even less than 0.5% of water, and especially free of water, the water not being added during the preparation of the composition but corresponding to the residual water provided by the mixed ingredients.

They may optionally be packaged in aerosol form and may be in the form of a mousse or a spray.

In the case of compositions in the form of oil-in-water or water-in-oil emulsions, the emulsification processes that may be used are of the paddle or impeller, rotor-stator and HPH type.

To obtain stable emulsions with a low content of polymer (oil/polymer ratio >25), it is possible to do the dispersion in concentrated phase and then to dilute the dispersion with the rest of the aqueous phase.

It is also possible, via HPH (between 50 and 800 bar), to obtain stable dispersions with drop sizes that may be as low as 100 nm.

The emulsions generally contain at least one emulsifier chosen from amphoteric, anionic, cationic and nonionic emulsifiers, used alone or as a mixture. The emulsifiers are appropriately chosen according to the emulsion to be obtained (W/O or O/W).

The compositions according to the invention are preferably in the form of an oil-in-water or water-in-oil emulsion. The emulsifying surfactants are chosen in an appropriate manner depending on the emulsion to be obtained.

Non-limiting examples of W/O emulsifying surfactants suitable for water-in-oil emulsions are especially given in the publication entitled *McCutcheon's Emulsifiers & Detergents,* 1998, International Edition, MC Publishing Company, in the chapter entitled HLB Index.

Examples of W/O emulsifying surfactants that may be mentioned include alkyl esters or ethers of sorbitan, of glycerol, of polyol or of sugars; silicone surfactants, for instance dimethicone copolyols, such as the mixture of cyclomethicone and of dimethicone copolyol, sold under the name DC 5225 C® by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R® by the company Goldschmidt, and the mixture of cetyldimethicone copolyol, of polyglyceryl isostearate (4 mol) and of hexyl laurate, sold under the name Abil WE 09® by the company Goldschmidt. One or more coemulsifiers may also be added thereto, which may be chosen advantageously from the group consisting of polyol alkyl esters.

Mention may also be made of non-silicone emulsifying surfactants, in particular alkyl esters or ethers of sorbitan, of glycerol, of polyol or of sugars.

Polyol alkyl esters that may in particular be mentioned include polyethylene glycol esters, for instance PEG-30 dipolyhydroxystearate, such as the product sold under the name Arlacel P135® by the company ICI.

Examples of glycerol and/or sorbitan esters that may be mentioned include polyglyceryl isostearate, such as the product sold under the name Isolan GI 34® by the company Goldschmidt; sorbitan isostearate, such as the product sold under the name Arlacel 987® by the company ICI; sorbitan glyceryl isostearate, such as the product sold under the name Arlacel 986® by the company ICI, and mixtures thereof.

For the O/W emulsions, examples of nonionic emulsifying surfactants that may be mentioned include polyoxyalkylenated (more particularly polyoxyethylenated and/or polyoxypropylenated) esters of fatty acids and of glycerol; oxyalkylenated esters of fatty acids and of sorbitan; polyoxyalkylenated (in particular polyoxyethylenated and/or polyoxypropylenated) esters of fatty acids, optionally in combination with an ester of fatty acid and of glycerol, such as the PEG-100 Stearate/Glyceryl Stearate mixture sold, for example, by the company ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by the company Henkel under the respective names Plantaren 2000® and Plantaren 1200®, cetostearyl glucoside, optionally as a mixture with cetostearyl alcohol, sold, for example, under the name Montanov 68® by the company SEPPIC, under the name Tegocare CG90® by the company Goldschmidt and under the name Emulgade KE3302® by the company Henkel, and arachidyl glucoside, for example in the form of the mixture of arachidyl and behenyl alcohols and of arachidyl glucoside sold under the name Montanov 202® by the company SEPPIC. According to a particular embodiment of the invention, the mixture of the alkylpolyglucoside as defined above with the corresponding fatty alcohol may be in the form of a self-emulsifying composition, for example as described in document WO-A-92/06778.

According to a particularly preferred form, the compositions are in the oil-in-water form.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

Another subject of the present invention consists of the use of the compositions according to the invention as defined above in the manufacture of products for the cosmetic treatment of the skin, lips, nails, hair, eyelashes, eyebrows and/or scalp, in particular care products, antisun products and makeup products.

The cosmetic compositions according to the invention can be used, for example, as makeup products.

Another subject of the present invention consists of a non-therapeutic cosmetic process for caring for and/or making up a keratin material, which consists in applying, to the surface of the said keratin material, at least one composition according to the invention as defined above.

The cosmetic compositions according to the invention may be used, for example, as care products and/or antisun products for the face and/or body with a liquid to semi-liquid consistency, such as milks, more or less smooth creams, cream gels or pastes. They may optionally be packaged in aerosol form and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", aerosol containers comprising a propellant and aerosol pumps using compressed air as propellant. These devices are described in patents U.S. Pat. Nos. 4,077,441 and 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

Assembly

According to another aspect, the invention also relates to a cosmetic assembly comprising:
i) a container delimiting one or more compartment(s), the said container being closed by a closing member and optionally being unsealed; and
ii) a makeup and/or care composition in accordance with the invention placed inside the said compartment(s).

The container may be, for example, in the form of a jar or a box.

The closing member can be in the form of a lid comprising a cap mounted so as to be able to move by translation or by pivoting relative to the container housing the said makeup and/or care composition(s).

The examples which follow serve to illustrate the invention without, however, exhibiting a limiting nature. In these examples, the amounts of the composition ingredients are given as weight percentages relative to the total weight of the composition.

EXAMPLES

Preparation Example A 100 g of perlite powder sold under the trade name GK-110 Thin® by the company Langfang Xindazhong Filter and the company Henan Zhongnan Filter Aid were placed in a flask equipped with a stirrer, and 150 g of titanium tetra-n-butoxide (Super Urecoat Industries) in the form of a suspension were added. The perlite was made to absorb the titanium precursor. An amount of 0.2 to 1 litre of water was then added to allow reaction for 1-8 hours at 30-100° C. Next, the suspension thus obtained was filtered, washed and dried to produce a composite powder of perlite coated with titanium dioxide.

In a second stage, 100 g of this composite powder were placed in a flask, and 150 g of titanium tetra-n-butoxide in suspension form were added. The composite was then made to absorb the titanium precursor. An amount of 0.2 to 1 litre of water was then added to allow reaction for 1-8 hours at 30-100° C. Next, the suspension thus obtained was filtered, washed and dried to produce a composite powder of perlite coated with titanium dioxide. Finally, a composite powder containing 40% by weight of titanium dioxide was obtained.

Preparation Example B

A composite powder based on perlite and titanium dioxide with a mean elementary size of less than 0.1 μm was prepared, under the same conditions as in Example A, using a perlite powder sold under the trade name Optimat 2550® by the company World Minerals.

Preparation Example C

A composite powder based on perlite and titanium dioxide was prepared, under the same conditions as in Example A, using a perlite powder sold under the trade name GK-110 Extra Thin by the company Langfang Xindazhong Filter and the company Henan Zhongnan Filter Aid.

Examples 1 to 4

The oil-in-water emulsions 1 to 4 were prepared according to the following protocol.
Preparation of the Emulsions The aqueous phase (A1, A2, A3) was prepared by mixing the starting materials with mechanical stirring at 65-70° C. The oily phase B1 was prepared by mixing the starting materials with mechanical stirring at 70-80° C. Phases B2 and B3 were added after cooling B1 to about 60-65° C. The solutions obtained are macroscopically homogeneous. The emulsion was prepared by slow introduction of the oily phase into the aqueous phase with stirring using a Moritz homogenizer at a stirring speed of 4500 rpm for 10 minutes. The oily phase C was added to the emulsion obtained with gentle stirring. The emulsion obtained was cooled to room temperature with slow stirring and phases D, E and F were then added. Phase G was added with stirring until the particles were visibly well dispersed. Finally, phase H was added with slow stirring. It was characterized by drops of between 1 μm and 10 μm in size.

The examples were compared with a particle content equal to 5%:

| Phase | Materials | Ex. 1* | Ex. 2* | Ex. 3* | Ex. 4 |
|---|---|---|---|---|---|
| A1 | Water | 42.00 | 42.00 | 42.00 | 42.00 |
| | Preserving agent | 0.40 | 0.40 | 0.40 | 0.40 |
| | Glycerol | 6.00 | 6.00 | 6.00 | 6.00 |
| | Propylene glycol | 6.00 | 6.00 | 6.00 | 6.00 |
| | Terephthalylidenecamphorsulfonic acid (Mexoryl SX ®) | 0.90 | 0.90 | 0.90 | 0.90 |
| | Triethanolamine | 0.16 | 0.16 | 0.16 | 0.16 |
| A2 | EDTA | 0.20 | 0.20 | 0.20 | 0.20 |
| A3 | Potassium cetyl phosphate (Amphisol K ®) | 1.00 | 1.00 | 1.00 | 1.00 |
| B1 | $C_{12}$-$C_{15}$-Alkylbenzoates (Finsolv TN ®) | 7.50 | 7.50 | 7.50 | 7.50 |
| | Octocrylene (Uvinul N539 T ®) | 7.00 | 7.00 | 7.00 | 7.00 |
| | Butylmethoxydibenzoyl methane (Parsol 1789 ®) | 3.00 | 3.00 | 3.00 | 3.00 |
| | Ethylhexyl triazone (Uvinul T150 ®) | 0.50 | 0.50 | 0.50 | 0.50 |
| B2 | Stearic acid | 1.00 | 1.00 | 1.00 | 1.00 |
| | Triethanolamine | 0.30 | 0.30 | 0.30 | 0.30 |
| | Glyceryl stearate (and) PEG-100 stearate (Arlacel 165 FL ®) | 1.00 | 1.00 | 1.00 | 1.00 |
| | Dimethylsiloxane | 0.50 | 0.50 | 0.50 | 0.50 |
| | Preserving agent | 0.30 | 0.30 | 0.30 | 0.30 |
| | Active agent | 0.10 | 0.10 | 0.10 | 0.10 |
| | 2-Phenoxyethanol | 0.70 | 0.70 | 0.70 | 0.70 |
| B3 | Titanium dioxide (and) aluminium hydroxide (and) stearic acid (MT 100TV ®) | 5.00 | | 2.00 | |
| C | Isohexadecane | 4.50 | 4.50 | 4.50 | 4.50 |
| | Acrylate/$C_{10}$-$C_{30}$-alkylacrylate copolymer (Pemulen TR-1 ®) | 0.25 | 0.25 | 0.25 | 0.25 |
| | Xanthan gum | 0.10 | 0.10 | 0.10 | 0.10 |
| D | Water | 1.00 | 1.00 | 1.00 | 1.00 |
| | Triethanolamine | 0.25 | 0.25 | 0.25 | 0.25 |
| E | Water | 6.34 | 6.34 | 1.34 | 6.34 |
| F | Tween 20 | 2.00 | 2.00 | 2.00 | 2.00 |
| | Perlite (Optimat 2550 ®) | — | 5 | 3 | |
| G | Composite particles of Example B | — | | | 5.00 |
| H | Alcohol | 2.00 | 2.00 | 2.00 | 2.00 |

*outside the invention

These compositions were evaluated according to the following properties:
  the matting effect using a glossmeter
  the greasy feel on application to the skin
Evaluation Protocols
Matting Effect The formulas are spread on a contrast card using a film spreader to a thickness of 100 μm. The cards are then dried for 24 hours at 37° C. After 24 hours, a solution of a mixture of oleic acid and water is vaporized onto the contrast cards. The shininess of the cards is then measured (60° angle) using a glossmeter.

Greasy Feel after Application to the Skin

The sensory impression after application of the formula to the skin is evaluated by applying the formula to a forearm in a proportion of 2 mg/cm². After a drying time equal to 2 minutes, the greasy feel between the fingers and at the surface of the forearm is observed and noted:
++ substantial greasy effect
+ presence of greasy effect
− absence of greasy effect In Vitro Protocol for Evaluating the Screening Efficacy The sun protection factor (SPF) is determined according to the "in vitro" method described by B. L. Diffey in J. Soc. Cosmet. Chem. 40, 127-133 (1989). The measurements were made using a UV-1000S spectrophotometer from the company Labsphere. Each composition is applied to a rough plate of PMMA, in the form of a homogeneous and even deposit in a proportion of 1 mg/cm$^2$.

Results

| Formula | Particles | Matting effect (gloss units) | in vitro SPF | Greasy feel |
|---|---|---|---|---|
| Example 1 Comparative | 5% loose TiO$_2$ particles | 47 ± 6.6 | 55.56 ± 10.6 | ++ |
| Example 2 Comparative | 5% loose perlite particles | 21.4 ± 2.8 | 25.28 ± 3.45 | − |
| Example 3 Comparative | 3% loose perlite particles + 2% loose TiO$_2$ particles | 31.2 ± 3.4 | 50.44 ± 8.66 | + |
| Example 4 (invention) | 5% TiO$_2$-perlite composite particles | 16.65 ± 2.2 | 41.40 ± 12.43 | − |

It was found that:

in Example 1 outside the invention, the use of loose TiO$_2$ particles without perlite produces, after application to the skin, substantial shininess and a strong greasy feel despite good photoprotective efficacy;

in Example 2 outside the invention, the use of loose perlite particles without titanium dioxide leads, after application to the skin, to a reduction in the shininess and the absence of a greasy feel, but leads to a substantial reduction in the photoprotective efficacy;

in Example 3 outside the invention, with an SPF comparable to that of Example 1, the use of the combination of loose perlite particles and of loose TiO$_2$ particles makes it possible to reduce the shininess, but with the presence of a greasy feel;

in Example 4 according to the invention, with an SPF comparable to that of Examples 1 and 3, the use of perlite-TiO$_2$ composite particles leads, surprisingly, after application to the skin, to a more substantial reduction in the shininess and to the absence of a greasy feel.

The invention claimed is:

1. Composite particles for screening out UV radiation, containing at least:
    i) a matrix comprising perlite particles, wherein the perlite particles have an untamped apparent density at 25° C. ranging from 10 to 400 kg/m$^3$ and
    ii) mineral UV-screening agent particles with a mean elementary size of less than 0.1 μm, wherein said particles of the mineral UV-screening agent are included in said matrix.

2. The particles according to claim 1, wherein the mineral UV-screening agent is chosen from metal oxides; the said metal oxides may optionally be treated with at least one surface-treatment agent.

3. The particles according to claim 1, wherein the mineral UV-screening agent is titanium dioxide (TiO$_2$).

4. The particles according to claim 1, wherein the perlite particles are in porous expanded form.

5. The particles according to claim 1, wherein the perlite particles have a particle size defined by a median diameter D$_{50}$ ranging from 0.5 to 50 μm.

6. The particles according to claim 1, wherein the perlite particles have a particle size distribution such that at least 50% of the particles are less than 20 μm in size.

7. The particles according to claim 1, wherein the perlite particles have a particle size distribution such that 90% by weight of the particles are less than 55 μm in size.

8. A composition containing, in a cosmetically acceptable medium, at least composite particles as defined according to claim 1.

9. A composition according to claim 8, which is in the form of a gel or a simple or complex emulsion, or in anhydrous form.

10. A cosmetic process for caring for and/or making up human keratin materials comprising at least the application, to the surface of the keratin material, of at least one composition as defined according to claim 8.

11. A non-therapeutic cosmetic process for limiting the darkening of the skin and/or improving the colour and/or uniformity of the complexion, comprising the application, to the surface of the keratin material, of a composition as defined according to claim 8.

12. A non-therapeutic cosmetic process for treating the signs of ageing of a keratin material, comprising the application, to the surface of the keratin material, of a composition as defined according to claim 8.

13. A cosmetic process for making the skin matt and/or for reducing its shininess and/or reducing the greasy effect, comprising the topical application, to the skin, of a composition as defined according to claim 8.

14. The particles according to claim 5, wherein the mineral UV-screening agent is chosen from metal oxides; the said metal oxides may optionally be treated with at least one surface-treatment agent.

15. The particles according to claim 1, wherein the mineral UV-screening agent is chosen from titanium, zinc or iron oxides or mixtures thereof; the said metal oxides may optionally be treated with at least one surface-treatment agent.

16. The particles according to claim 2, wherein the mineral UV-screening agent is titanium dioxide (TiO$_2$).

17. The particles according to claim 2, wherein the perlite particles are in porous expanded form.

18. The particles according to claim 3, wherein the perlite particles are in porous expanded form.

19. The composition according to claim 8 which is in the form of an oil-in-water emulsion characterized by drops of 1 to 10 μm in size.

* * * * *